United States Patent [19]
Bristoll et al.

[11] 3,934,451
[45] Jan. 27, 1976

[54] METHOD OF DETECTING IMPERFECTIONS IN A HEAT-INSULATING LINING

[75] Inventors: Paul Bristoll; Godefridus Arink, both of Amsterdam, Netherlands

[73] Assignee: Shell Oil Company, Houston, Tex.

[22] Filed: May 29, 1973

[21] Appl. No.: 364,394

[30] Foreign Application Priority Data
June 2, 1972   Netherlands........................ 7207473

[52] U.S. Cl. .............................................. 73/15 FD
[51] Int. Cl.² ............................................ G01N 25/72
[58] Field of Search ...... 73/15 R, 15 FD, 15.4, 104; 220/9 LG

[56]               References Cited
                UNITED STATES PATENTS

| | | |
|---|---|---|
| 2,764,889 | 10/1956 | Hughes et al. ...................... 73/15.4 |
| 3,433,052 | 3/1969 | Maley ..................................... 73/15 |
| 3,462,602 | 8/1969 | Apple .............................. 73/351 X |
| 3,596,519 | 8/1971 | Blonder et al. ......................... 73/15 |
| 3,655,086 | 4/1972 | Tenner..................................... 220/9 |
| 3,688,558 | 4/1972 | Tixler..................................... 73/15 |
| 3,757,982 | 9/1973 | Isenberg............................ 220/9 X |
| 3,802,948 | 4/1974 | Noma ............................... 220/9 X |

FOREIGN PATENTS OR APPLICATIONS

| | | | |
|---|---|---|---|
| 142,457 | 9/1960 | U.S.S.R. ................................ 73/15 |
| 136,077 | 4/1960 | U.S.S.R. ................................ 73/15 |
| 171,632 | 11/1965 | U.S.S.R. ................................ 73/15 |

*Primary Examiner*—Herbert Goldstein

[57]               ABSTRACT

A method of detecting imperfections in a heat-insulating lining of foamed material of the wall of a space suitable for cryogenic uses by cooling the surfaces of the lining by scanning with a jet of cooled gas and observing the lining for imperfections in the cooled state.

6 Claims, No Drawings

METHOD OF DETECTING IMPERFECTIONS IN A HEAT-INSULATING LINING

BACKGROUND OF THE INVENTION

Spaces within tanks or lines can be properly insulated against penetration of heat by one or more layers of foamed material on the inner surface of the walls. By foamed material is here meant a material having a cellular structure, the cells of which being open or closed. The material is preferably rigid. Suitable materials are organic foams which may be applied to the wall by spraying, such as polyurethane foam. The insulating lining is composed of adjacent strips and also often of several layers on top of each other. Other materials such as impermeable membranes may be used beneath and between the layers.

During use, cryogenic linings come into contact with cold liquid. As the result of cooling there is substantial shrinkage, with the result that cracks may occur in the foamed material. This problem becomes more acute as the liquid is colder, such as for example, with liquefied methane, natural gas or nitrogen. The occurrence of cracks as the result of shrinkage is promoted by hair cracks already present or by incomplete adhesion of adjacent strips of the foamed material, and it is of great importance to detect this imperfection in order to repair it before the space is taken into use. The present invention provides a method of so doing.

SUMMARY OF THE INVENTION

The present invention therefore relates to a method of detecting imperfections in a heat-insulating lining of foamed material of the walls of a space suitable for cyrogenic uses, in which the surface of the lining is temporarily and locally cooled by scanning with a jet of cooled gas and is evaluated for imperfections in that condition.

Within the framework of the above described method, the present invention not only solves the above mentioned problems of the prior art, but also achieves further significant advantages as will be apparent from the description of preferred embodiments following.

DESCRIPTION OF THE PREFERRED EMBODIMENTS

A very superficial cooling is sufficient to make an imperfection in a formed lining visible as a split, since the materials concerned are good heat-insulation materials. Scanning with a cooling agent may therefore be carried out rapidly. Evaluation can be done visually and should be effected immediately since any split formed disappears again when the material warms up, although the imperfection remains present. A simple and effective method involves immediately marking a split which has become visible so that the spots which must be repaired can be traced. Evaluation may also be effected with the aid of photographs taken immediately after cooling. An imperfection can then be located from the photographs, for example with the aid of a system of co-ordinates or of a pattern of marks already present. The latter method is very suitable for automatic inspection. Photographing may also be considered for inspection of less readily accessible linings.

A suitable cooled gas is vapor of liquid nitrogen. A nozzle may be connected with a flexible line to a storage tank with liquid nitrogen. A stream of cold gas may be provided by passing through air or nitrogen gas or by heating the liquid nitrogen.

It has been found that a tank aboard a ship for the transport of liquid natural gas by sea can be inspected in approximately three days by one man who systematically scans the lining manually with the nozzle and simultaneously provides marks at splits which become visible. The vessel with liquid nitrogen may be mounted on deck.

We claim as our invention:

1. A method of detecting imperfections in a heat-insulating lining of foamed material of a wall enclosing a space suitable for cryogenic uses, comprising locally cooling the surface of the lining by scanning with a jet of cooled gas and observing the lining for imperfections in the cooled state.

2. The method of claim 1 comprising utilizing vapors of liquid nitrogen for cooling.

3. The method of claim 1 including photographing the imperfections in the cooled state for marking purposes.

4. The method of claim 1 including marking the imperfection while it remains visible in the cooled state.

5. A method for detecting a crack or split in a foamed lining on the inner surface of a wall of a tank utilized for transporting a cold liquid comprising temporarily and locally cooling the surface of the foamed lining with a jet of cooled gas in order to cause the surface to contract and thereby render the crack or split visible without magnification and marking the crack or split while it remains visible.

6. A method for detecting a crack or split in a foamed plastic material in which the crack or split enlarges upon cooling of the material by subjecting the material to temporary and local cooling whereby the crack or split becomes visible as the plastic material shrinks and the crack or split widens, and marking the crack or split while the plastic is in the cooled state.

* * * * *